United States Patent [19]

Briet et al.

[11] 4,201,783

[45] May 6, 1980

[54] ANTIDEPRESSANT SUBSTITUTED HEXAHYDRO BENZOPYRANO [3,2-C] PYRIDINES

[75] Inventors: Philippe Briet; Jean-Jacques Berthelon; Jean-Claude Depin, all of Lyons, France

[73] Assignee: Lipha Lyonnaise Industrielle Pharmaceutique, Lyons, France

[21] Appl. No.: 918,597

[22] Filed: Jun. 23, 1978

[30] Foreign Application Priority Data

Jun. 24, 1977 [FR] France .................................. 77 19360
Jun. 1, 1978 [FR] France .................................. 78 16376

[51] Int. Cl.² .................. A61K 31/445; C07D 491/18
[52] U.S. Cl. ................................. 424/256; 542/404; 546/48; 546/63; 546/216; 546/221
[58] Field of Search .................. 260/293.55; 424/256; 546/63, 48; 542/404

[56] References Cited

U.S. PATENT DOCUMENTS

| | | | |
|---|---|---|---|
| 3,673,194 | 6/1972 | Morlock et al. | 260/293.55 |
| 4,070,360 | 1/1978 | Ten Broeke et al. | 260/293.55 |

OTHER PUBLICATIONS

Sammour, A. et al., *Indian J. Chem.*, 12, 51–53 (1974).

*Primary Examiner*—Henry R. Jiles
*Assistant Examiner*—Richard A. Schwartz
*Attorney, Agent, or Firm*—Browdy and Neimark

[57] ABSTRACT

Substituted hexahydro benzopyrano [3,2-c] pyridines, useful as antidepressants, have the formula

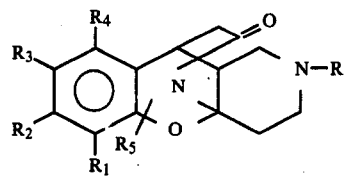

where R is hydrogen or a saturated or unsaturated, linear or branched, lower alkyl, or an aralkyl, acyl, dialkylaminoalkyl, carbonylalkyl, alkoxycarbonyl, haloalkoxycarbonyl or aryl radical; $R_1$ is hydrogen, halogen, or lower alkoxy; $R_2$ is hydrogen or halogen; $R_3$ is hydrogen, halogen, lower alkyl, alkoxy nitro or amino, or forms naphthalene with $R_4$ and the benzene ring; $R_4$ is hydrogen, a halogen, or forms naphthalene with $R_3$ and the benzene ring; $R_5$ is hydrogen, lower alkyl, or aralkyl.

21 Claims, No Drawings

ANTIDEPRESSANT SUBSTITUTED HEXAHYDRO BENZOPYRANO [3,2-C] PYRIDINES

FIELD OF THE INVENTION

The present invention relates to substituted hexahydrobenzopyrano[3,2-c] pyridines.

BACKGROUND OF THE INVENTION

From the article by A. Sammour and M. Alkady (Indian Journal of Chemistry, Vol. 12, pp. 51-53), it is known to condense ketones, cyclohexanone for example, on 3-carbethoxycoumarins to obtain 2-amino-2,3 cyclohexanechroman-4-α-carbamidoacetic acid lactam.

SUMMARY OF THE INVENTION

Hexahydrobenzopyrano[3,2-c] pyridines have been found, represented by the formula:

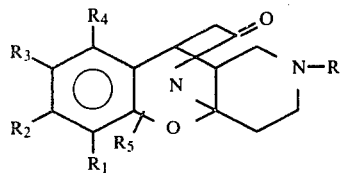

where R is hydrogen or a saturated or unsaturated, linear or branched, lower ($C_1$-$C_6$) alkyl radical, or an aralkyl, acyl, dialkylaminoalkyl, carbonylalkyl, alkoxycarbonyl, haloalkoxycarbonyl, or aryl radical; $R_1$ is hydrogen, a halogen, or a lower ($C_1$-$C_6$) alkoxy radical; $R_2$ is hydrogen or a halogen; $R_3$ is hydrogen, a halogen, a lower ($C_1$-$C_6$) alkyl radical, an alkoxy, a nitro, or amino group, or forms naphthalene with $R_4$ and the benzene ring; $R_4$ is hydrogen, a halogen, or forms naphthalene with $R_3$ and the benzene ring; $R_5$ is hydrogen, a lower ($C_1$-$C_6$) alkyl radical, or an aralkyl radical.

The salts of these new compounds with mineral and organic acids which are acceptable for the treatment of human beings constitute part of the invention.

These compounds possess remarkable pharmacological properties which render them useful in human medicine, especially for the treatment of depression and mental problems.

DETAILED DESCRIPTION OF EMBODIMENTS

The polycyclic structure of these compounds indicates that a given compound will have several stereoisomers. Thinlayer chromatography of the reaction products reveals the existence of two stereoisomers, A and B. Recrystallization in an appropriate solvent is sufficient to isolate, in the pure state, the predominent stereoisomer from the crude reaction product. The minor stereoisomer can be obtained by concentrating the mother liquors. The minor stereoisomer can be transformed into the major stereoisomer by acid treatment.

It has been demonstrated that certain compounds possess two stereoisomers, A and B. Consequently, two methods of synthesis are used for these compounds, allowing either series A or series B to be produced.

The preparation processes are illustrated in the following sequence, where R, $R_1$, $R_2$, $R_3$, $R_4$ and $R_5$ have the meanings given above.

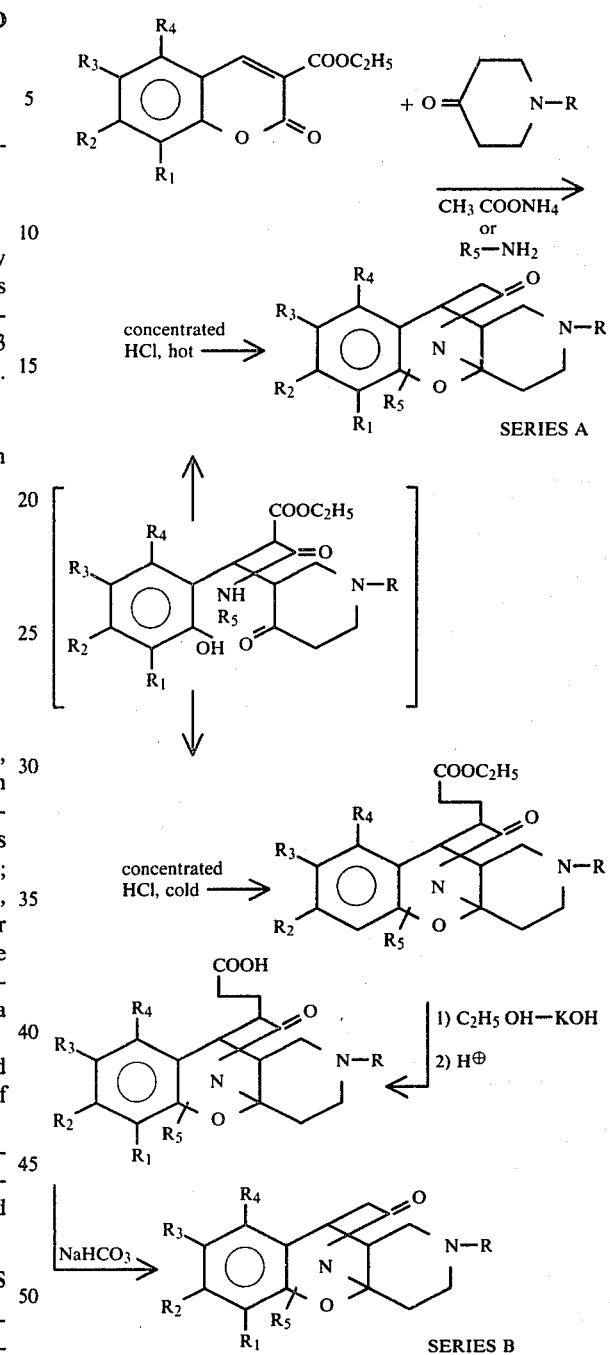

The Michael addition of an N-substituted 4-piperidone to an ethyl coumarin-3-carboxylate and the opening of the resultant adduct by ammonium acetate, which generates ammonia, or by a primary amine $R_5$—$NH_2$, is accomplished by heating the compounds together at temperatures between 20° and 200° C. with or without an alcohol solvent for times varying from 3 to 70 hours. Treatment with boiling concentrated hydrochloric acid produces Series A compounds by dehydrating cyclization. On the other hand, processing with cold concentrated hydrochloric acid permits isolation of a β-keto ester, hydrolyzable by the potash-alcohol pair to the corresponding acid.

Decarboxylation by heating in sodium bicarbonate allows Series B compounds to be isolated. The change of Series B compounds to the corresponding Series A compounds can be accomplished by treating such Series B compound with hot hydrochloric acid.

convenient to replace this hydrogen by a saturated or unsaturated, linear or branched, alkyl radical or an aralkyl or dialkylaminoalkyl radical:

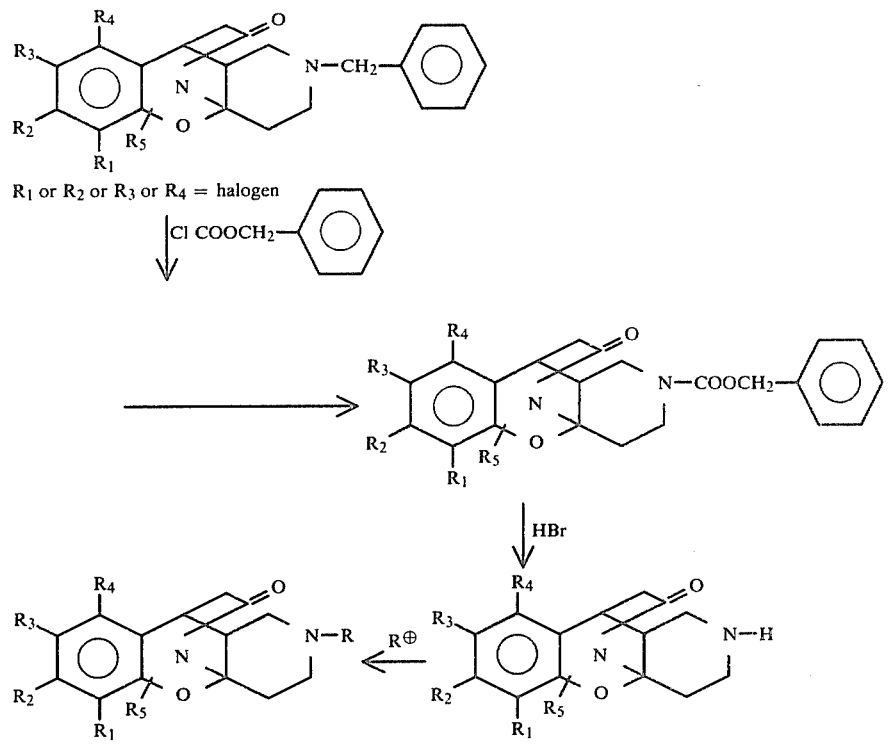

According to one version of the process, when R is hydrogen, a previously obtained compound, especially R=benzyl, can be treated by catalytic hydrogenation, after which the hydrogen can be replaced by a saturated or unsaturated, linear or branched, alkyl radical or an aralkyl or dialkylaminoalkyl radical.

According to another version, a compound where R is an alkyl such as methyl, or an aralkyl such as benzyl, can be treated with a chlorocarbamate by boiling in an aromatic solvent, thus isolating the compounds in which R is an alkoxycarbonyl:

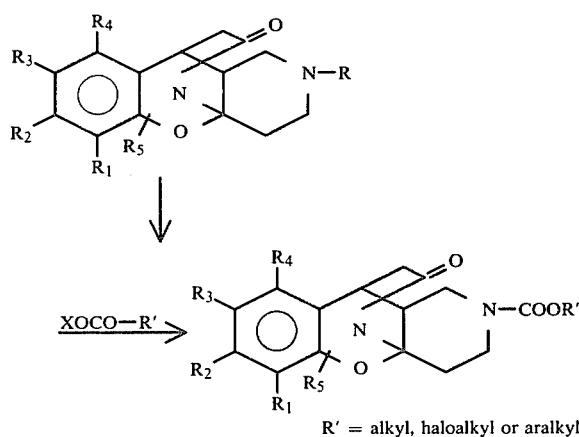

R' = alkyl, haloalkyl or aralkyl

When $R_1$ or $R_2$ or $R_3$ or $R_4$ is a halogen, it is possible to treat a compound where R=benzyl with benzyl chloroformate and to hydrolyze the carbamate obtained with hydrobromic acid to obtain compounds where R is H when $R_1$ or $R_2$ or $R_3$ or $R_4$ is a halogen. It is then In particular, to obtain compound described in the example 34 where $R_3$ =Cl and R, $R_1$, $R_2$, $R_4$, $R_5$ are hydrogen, it is advantageous to condense the ethyl 6-chloro coumarin-3-carboxylate with 4-piperidone hydrochlorid monohydrate according to the general process previously described.

The ethyl halocoumarin-3-carboxylates, intermediates of the synthesis, such as ethyl 6-fluoro coumarin-3-carboxylate, ethyl 5-chloro coumarin-3-carboxylate and ethyl 7-chloro coumarin-3-carboxylate are novel, and for this reason come within the scope of the invention.

The novel substituted hexahydro benzopyrano [3,2-c] pyridines possess remarkable properties which make them useful as medicines for treating depression and mental problems. This mood-altering activity can be determined by standard, routine tests well known specialists. Thus, the compounds according to the invention have been found to be powerful inhibitors of ptosis with reserpine.

In Swiss mice, a compound was administered orally simultaneously with reserpine given interperitoneally at a dose of 5 mg/kg. Ptosis measured according to B. Rubin et al. (J. Pharmacol. Exp. Therap., pp 120-125, 1957) one hour, 1.5 hours, and 2 hours later, permitted determination of the dose which would inhibit ptosis by an average of 50%. Table I lists the doses which were effective in 50% of the cases ($ED_{50}$) obtained for several products, and those obtained for the standard substances well known to specialists, such as imipramine, i.e. [N-(3-dimethylaminopropyl) iminodibenzyl hydrochloride], and amitriphthyline, i.e. (3-dimethylamino propylidene-5-dibenzo [a,d] 1,4-cycloheptadiene hydrochloride).

TABLE I

| Products | ED$_{50}$, mg/kg |
| --- | --- |
| Imipramine | 2.9 |
| Amitriphthyline | 10 |
| Example 1 A | 6 |
| Example 1 B | 24 |
| Example 5 A | 0.04 |
| Example 5 B | 11 |
| Example 6 | 0.1 |
| Example 7 | 3.5 |
| Example 8 | 1 |
| Example 9 | 5 |
| Example 10 | 1.8 |
| Example 15 | 0.6 |
| Example 18 | 0.67 |
| Example 27 | 0.37 |
| Example 28 | 0.25 |
| Example 36 | 0.7 |

Toxicity was determined in Swiss mice, as well as the doses lethal to 50% of the animals (LD$_{50}$), administered orally. The values are given in the Table below:

TABLE II

| Products | LD$_{50}$, administered orally, mg/kg |
| --- | --- |
| Imipramine | 330 |
| Amitriphthyline | 150 |
| Example 1 A | 2,700 |
| Example 1 B | 600 |
| Example 5 A | 360 |
| Example 5 B | 2,000 |
| Example 6 | 720 |
| Example 7 | 1,200 |
| Example 8 | 1,080 |
| Example 9 | >3,200 |
| Example 10 | 600 |
| Example 15 | 2,470 |
| Example 18 | 1,200 |
| Example 27 | >1,600 |
| Example 28 | 1,100 |
| Example 36 | 600 |

The medication, containing as the active principle a compound according to the invention, combined with an appropriate pharmaceutical vehicle or expedient, is given in an appropriate form for oral or parenteral administration.

The forms of administration are, for example, tablets, capsules, gelatin-coated pills, or ampoules; these posological forms contain 0.05 to 100 mg of the active substance and permit a daily dosage of 1 to 200 mg.

EXAMPLES

— 100 mg tablet, coated if desired:

EXAMPLES

| 100 mg tablet, coated if desired: | |
| --- | --- |
| Active principle | 5 mg |
| Lactose | 41 mg |
| Wheat starch | 41 mg |
| Gelatin | 2 mg |
| Alginic acid | 5 mg |
| Talc | 5 mg |
| Magnesium stearate | 1 mg |
| Composition of a gelatin-coated capsule: | |
| Active principle | 2 mg |
| Lactose | 30 mg |
| Wheat starch | 35 mg |
| Talc | 2.5 mg |
| Magnesium stearate | 0.5 mg |
| Composition of an injectable solution: | |
| Active principle | 5 mg |
| Sodium chloride | 18 mg |
| Water for injectable preparation | |

EXAMPLES-continued

| | |
| --- | --- |
| to bring to | 2 ml |

The following are observations recorded during a clinical test of the medication containing the active compound of Example 5 A.

CASE NO. 1

Name: Dac . . . Agnes
Age: 78
Sex: F
Diagnosis: pre-senile depression
Associated treatments: NOZINAN-SUREPTIL
Dosage and duration of treatment: 5 mg daily for 30 days
Activity:
Weight gain. Improvement of mood and sociability.
Tolerance:

| . Clinical | } | N.A.D. |
| --- | --- | --- |
| . Biological | | |

CASE NO. 2

Name: Lar . . . Gineste
Age: 58
Sex: M
Diagnosis:
Post-neuroleptic depression with schizophrenia.
Associated treatment: NOZINAN-ARTANE-GARDENAL
Dosage and duration of Treatment: 20 mg daily for 30 days
Activity:
Weight gain. Improvement of mood and sleep. Reduced anxiety. Relief of hypochondriac complaints.
Tolerance:

| . Clinical | } | N.A.D. |
| --- | --- | --- |
| . Biological | | |

CASE NO. 3
Name: Jac. . . Marcel
Age: 55
Sex: M
Diagnosis:
Serious hypochondriac depressive syndrome.
Associated treatment: MEPRONIZINE
Dosage and duration of treatment: 10 mg daily for 20 days
Activity:
The patient was less preoccupied with his body. Decrease of compulsive washing. Improvement of social behavior.
Tolerance:

| . Clinical | } | N.A.D. |
| --- | --- | --- |
| . Biological | | |

CASE NO. 4
Name: Mic. . . Louise
Age: 55

Sex: F
Diagnosis:
 Melancholic depressive relapse
Associated treatment: NOZINAN 25 mg
Dosage and duration of treatment: 25 mg daily for 45 days
Activity:
 Improvement of mood. Less pessimistic attitude. Less frequent crying. Less pronounced feeling of guilt.
Tolerance:

| . Clinical | } N.A.D. |
|---|---|
| . Biological | |

CASE NO. 5

Name: Til. . . Francois
Age: 47
Sex: M
Diagnosis:
 Depressive syndrome in an alcoholic of the melancholic type.
Associated treatment: Injection of multiple vitamins, NOZINAN (50 mg), ARTANE 5.
Dosage and duration of treatment: 5 mg daily for 30 days.
 Improvement of mood. Less frequent crying. Improved appetite.
Tolerance:
 Clinical: slight dizziness and nausea.
 Biological: N.A.D.

CASE NO. 6

Name: Bel. . . Andre
Age: 45
Sex: M
Diagnosis:
 Hypochondriac delirium with anxiety.
Associated treatment: ARTANE 10 mg ANTASTHENE.
Dosage and duration of treatment: 25 mg daily for 30 days.
Activity:
 Decrease of hypochondriac complaints. Patient less irritable and apprehensive.
Tolerance.
 Clinical: slight vertigo
 Biological: N.A.D.

The following are examples of the preparation of the compounds according to the invention:

EXAMPLE 1

4a-amino-2-methyl-1,2,3,4,4a,10a-hexahydro [10 H] benzopyrano-[3,2-c]pyrid-10-yl acetic acid lactam $C_{15}H_{18}N_2O_2$ Molecular weight=258.31.

2.182 kg (10 moles) ethyl coumarine-3-carboxylate, 1.144 kg (10 moles) N-methyl 4-piperidone, was dissolved in 35 L of anhydrous ethanol; 1.544 kg (20 moles) of ammonium acetate were added, and the mixture of reactants was agitated for 72 hours at ambient temperature. The mixture was then refluxed for one hour, evaporating approximately 25 L of ethanol. The resinous material was then dissolved in 8.9 L of concentrated hydrochloric acid, and refluxed for ½ hour. The mixture of reactants was then cooled using an ice bath, and adjusted to an alkaline pH with 9 L of 30% NaOH. The resultant solid was dried and was in the form of a creamy product which melted at 228° C. It was recrystallized in 10 L of isopranol. The result was 2.083 kg (Yield 70%) of 4a-amino-2-methyl-1,2,3,4,2a,10a-hexahydro [10 H] benzopyrano-[3,2-c]pyrid-10-yl acetic acid lactam (Product A), $MP_G=224°$ C., $IR\nu_{C=O}$: 1690 cm$^{-1}$.

| Analysis: | C% | H% | N% |
|---|---|---|---|
| Calculated | 69.74 | 7.02 | 10.85 |
| Found: | 69.62 | 6.97 | 10.85 |

Hydrochloride: $MP_G=250°-252°$ C. (ethanol).

TLC alkaline plate, 0.1 N silica gel, elutant: methanol chloroform-cyclohexane (1-3-5): 1 spot. Concentration of the mother liquors produced Product B: $MP_G=232°-234°$ C., $IR\nu_{C=O}$: 1680 cm$^{-1}$.

| Analysis: | C% | H% | N% |
|---|---|---|---|
| Calculated: | 69.74 | 7.02 | 10.85 |
| Found: | 69.72 | 6.90 | 10.70 |

Conversion of B to A: reflux 10 g of B for one hour in 100 mL of concentrated hydrochloric acid. After cooling, adjust pH toward the basic side using 30% NaOH, extract with $CH_2Cl_2$, dry on $Na_2SO_4$, evaporate the solvent. The result is a white solid physical/chemical characteristics are identical to those of A.

EXAMPLE 2

4a-amino-2-benzyl-1,2,3,4,4a,10a-hexahydro[10H]benzopyrano [3,2-c]pyrid-10-ylacetic acid lactam.

$C_{21}H_{22}N_2O_2$, molecular weight=334.42.

Prepared according to Example 1, using 47.6 g (0.218 mole) ethyl coumarine-3-carboxylate, 33.4 g (0.218 mole) N-benzyl-4-piperidone, 34.8 g (0.436 mole) ammonium acetate, in 1.9 L of anhydrous ethanol. The yield is 43.7 g (60%) 4a-amino-2-benzyl-1,2,3,4,4a,10a-hexahydro[10H]benzopyrano[3,2-c]pyrid-10-ylacetic acid lactam in the form of a white solid $MP_G=192°$ C. (ethanol).

Hydrochloride: $C_{21}H_{23}ClN_2O_2$, molecular weight=370.87,
$MP_G=254°-255°$ C. (methanol) $IR\nu_{C=O}$: 1680 cm$^{-1}$.

| Analysis: | C% | H% | N% | Cl% |
|---|---|---|---|---|
| Calculated: | 68 | 6.25 | 7.55 | 9.56 |
| Found: | 68.32 | 6.53 | 7.84 | 9.61 |

EXAMPLE 3

4a-amino-2-methyl-6-methoxy-1,2,3,4,4a,10a-hexahydro[10 H]benzopyrano[3,2-c]pyrid-10-ylacetic acid lactam.

$C_{16}H_{20}N_2O_3$, molecular weight=288.35

Prepared according to Example 1, using 93 g (0.375 mole) 8-methoxy-3-carbethoxycoumarin, 30.6 g (0.375 mole) N-methyl-4-piperidone, 41.4 g (0.75 mole) ammonium acetate, and 3.6 L of alcohol. The yield is 48.6 g (45%) 4a-amino-2-methyl-6-methoxy-1,2,3,4,4a,10a-hexahydro[10 H]benzopyrano[3,2-c]pyrid-10-ylacetic acid lactam in the form of a white solid $MP_G=258°$ C.

Hydrochloride, monohydrate: $C_{16}H_{23}ClN_2O_4$, molecular weight 342.82. $MP_G=265°$ C. (methanol) $IR\nu_{C=O}$: 1680 cm$^{-1}$ $IR\nu_{-OH}=3.500$ cm$^{-1}$

| Analysis: | C% | H% | Cl% | N% |
|---|---|---|---|---|
| Calculated: | 56.04 | 6.76 | 10.34 | 8.17 |
| Found: | 56.23 | 6.39 | 10.60 | 8.09 |

EXAMPLE 4

4a-amino-1,2,3,4,4a,10a-hexahydro[10 H]benzopyrano[3,2-c]pyrid-10-ylacetic acid lactam $C_{14}H_{16}N_2O_2$ molecular weight=244.30.

34.3 g of the product of Example 2 are dissolved in 320 mL of ethanol and stored for 5 hours at 60° C. under an initial hydrogen pressure of 60 kg in the presence of 4.7 g of 10% Pd/C.

After cooling, filtering of the catalyst, and evaporation of the solvent, 4a-amino-1,2,3,4,4a,10a-hexahydro[10 H]benzopyrano[3,2-c]pyrid-10-ylacetic acid lactam is obtained in the form of a white solid melting at 212° C.

Weight obtained=20 g(Yield: 80%). $IR\nu_{C=O}$: 1680 cm$^{-1}$.

Hydrochloride: $C_{14}H_{17}ClN_2O_2$, molecular weight=280.76, $MP_G=292°-294°$ C. (methanol).

| Analysis: | C% | H% | N% | Cl% |
|---|---|---|---|---|
| Calculated: | 59.89 | 6.10 | 9.98 | 12.63 |
| Found: | 59.71 | 6.18 | 9.87 | 12.38 |

EXAMPLE 5

4a-amino-8-chloro-2-methyl-1,2,3,4,4a,10a-hexahydro[10 H]benzopyrano[3,2c]pyrid-10-ylacetic acid lactam $C_{15}H_{17}ClN_2O_2$, molecular weight=292.77.

5.1. Product A

Refluxing was carried out for 8 hours with 101.06 g (0.4 mole) ethyl-6-chlorocoumarin-3-carboxylate, 45.76 g (0.4 mole) N-methyl-4-piperidone, 61.7 g (0.8 mole) ammonium acetate, and 12 L of ethanol. The solvent was evaporated and the residue dissolved in 320 mL of concentrated hydrochloric acid, with the resultant solution being refluxed for ½ hour. The solution was then made alkaline with 30% NaOH, cooling the medium in an ice bath. The solution was then diluted with H$_2$O and extracted with chloroform. After drying over Na$_2$SO$_4$ and evaporation, the result was 148 g of a beige solid. This was recrystallized in the acetone-methanol mixture. The result was 55 g of 4a-amino-8-chloro-2-methyl-1,2,3,4,4a,10a-hexahydro[10 H]benzopyrano[3,2-c]pyrid-10-ylacetic acid lactam(Yield: 47%) $MP_G=245°$ C. $IR\nu_{C=O}$: 1680 cm$^{-1}$

| Analysis: | C% | H% | Cl% | N% |
|---|---|---|---|---|
| Calculated: | 61.53 | 5.85 | 12.11 | 9.57 |
| Found: | 61.76 | 5.83 | 12.01 | 9.56 |

Hydrochloride: $C_{15}H_{18}Cl_2N_2O_2$, molecular weight=329.22 $MP_G=260°-262°$ C. (ethanol).

Methanesulfonate: 10 g of the product of Example 5.1 is dissolved in the required quantity of chloroform in 60° C. This is cooled to 40° C. and 2.5 mL of methanesulfonic acid dissolved in 7.5 mL of chloroform. Cooling produces a white product which is dried and recrystallized in methanol, $MP_G=265°-267°$ C.

| Analysis: | C% | H% | Cl% | N% |
|---|---|---|---|---|
| Calculated: | 49.42 | 5.44 | 9.12 | 7.20 |
| Found: | 49.29 | 5.45 | 8.95 | 7.13 |

5.2 Product B 5.2.1: Lactam of the ethyl monoester of 4a-amino-8-chloro-2-methyl-1,2,3,4,4a,10a-hexahydro[10 H]benzopyrano[3,2-c]pyrid-10-ylmalonic acid $C_{18}H_{21}ClN_2O_4$, molecular weight=364.827.

Refluxing was performed for 8 hours with 80 g (0.31 mole) of ethyl 6-chlorocoumarin-3-carboxylate, 35.8 g (0.31 mole) N-methyl-4-piperidone, 48.8 g (0.62 mole) ammonium acetate and 1240 mL ethanol. After evaporation, the residue is dissolved in 600 mL of concentrated hydrochloric acid (cold), and agitated for 1 hour. The pH is adjusted to the alkaline side by adding 600 mL of 30% soda and 600 g of ice, keeping the temperature below 25° C. Two extractions are performed, using 1 L of chloroform each time. The organic phase is dried over sodium sulfate and evaporated. Recrystallization of the resultant residue from ethanol results in the isolation of 63 g of the anticipated product, with a yield of 56%, $MP_G=190°$ C.

5.2.2. 4a-amino-8-chloro-2-methyl-1,2,3,4,4a,10a-hexahydro[10 H]benzopyrano[3,2-c]pyrid-10-ylmalonic acid lactam.

A solution consisting of 21 g (0.375 mole) of potash in 400 mL of water is added to a suspension of 53 g (0.15 mole) of the product of Example 5.21. in 400 mL of ethanol. The mixture is then refluxed for one hour. The solution is then cooled to 12° C. and adjusted to pH 5-6 by adding N-hydrochloric acid. The solution is then allowed to stand overnight and the precipitate is dried. This results in 35 g of the anticipated product, with a yield of 75.5%. The melting point is 210°-215° C. with decomposition.

5.2.3. Product B 10 g (0.03 mole) of the product of Example 5.2.2 is added to a solution of 2.5 g (0.03 mole) of sodium becarbonate in 100 mL of water, and refluxed for 1 hour. A precipitate forms gradually. The solution is then cooled and dried. Recrystallization from ethyl alcohol produces 4.1 g of Product B:

Melting point$_G=246°$ C., $IR\nu_{C=O}$: 1700 cm$^{-1}$

| Analysis: | C% | H% | N% |
|---|---|---|---|
| Calculated | 61.53 | 5.83 | 9.57 |
| Found | 61.36 | 5.85 | 9.63 |

EXAMPLE 6

4a-amino-8-bromo-2-methyl-1,2,3,4,4a,10a-hexahydro[10 H]benzopyrano[3,2-c]pyrid-10-ylacetic acid lactam $C_{16}H_{20}N_2O_2$ Molecular weight=272.34.

This is prepared according to Example 5.1 beginning with 47 g (0.158 mole) of ethyl 6-bromocoumarin-3-carboxylate, 18.1 g (0.158 mole) of N-methyl-4-piperidone, 24.4 g (0.316 mole) ammonium acetate, and 3 L of ethanol. After recrystallization from the acetone-ethanol mixture, 26 g of 4a-amino-8-bromo-2-methyl- 1,2,3,4,4a,10a,hexahydro[10 H]benzopyrano[3,2-c]pyrid-10-ylacetic acid lactam is obtained. (Yield=49%)
Melting point $_G$=237°-239° C. IR$\nu_{C=O}$: 1690 cm$^{-1}$.

| Analysis: | C% | H% | Br% | N% |
|---|---|---|---|---|
| Calculated: | 53.42 | 5.08 | 23.70 | 8.31 |
| Found: | 53.60 | 5.08 | 23.87 | 8.40 |

EXAMPLE 7

4a-amino-28-dimethyl-1,2,3,4,4a,10a-hexahydro[10 H]benzopyrano[3,2-c]pyrid-10-ylacetic acid lactam $C_{16}H_{20}N_2O_2$ Molecular weight=272.34

Prepared according to Example 5.1, beginning with 60 g (0.258 mole) of ethyl 6-methylcoumarin-3-carboxylate, 29.6 g (0.258 mole) N-methyl-4-piperidone, 39.9 g (0.516 mole) ammonium acetate and 2 L of ethanol. After recrystallization from the acetone-ethanol mixture, the result was 39.3 g of 4a-amino-28-dimethyl-1,2,3,4,4a,10a-hexahydro[10 H;]benzopyrano [3,2-c]pyrid-10-ylacetic acid lactam. (Yield: 56%) Melting point$_G$=241°-243° C.
IR$\nu_{C=O}$: 1680 cm$^{-1}$.

| Analysis: | C% | H% | N% |
|---|---|---|---|
| Calculated | 70.56 | 7.40 | 10.29 |
| Found | 70.58 | 7.41 | 10.38 |

EXAMPLE 8

4a-amino-8-fluoro-2-methyl-1,2,3,4,4a,10a-hexahydrol[10 H]benzopyrano[3,2-c]pyrid-10-ylacetic acid lactam $C_{15}H_{17}FN_2O_2$ Molecular weight=276.31

8.1 - Ethyl 6-fluorocoumarin-3-carboxylate $C_{12}H_9FO_4$ Molecular weight=236.19.

77 g (0.55 mole) 4-fluoro-2-hydroxybenzaldehyde, 96.6 g (0.604 mole) ethyl malonate, 220 Ml ethanol, 2.9 mL piperidine and 0.3 mL of glacial acetic acid are refluxed for 3 hours. The mixture is then poured into 600 mL of ice water. The mixture is then filtered and the ethyl 6-fluorocoumarin-3-carboxylate is recrystallized from ethanol: melting point=108° C., IR$\nu_{C=}$:1710 cm$^{-1}$ (lactone), 1730 cm$^{-1}$ (ester) NMR (CDCl$_3$)$\delta$ ppm relative to TMS.

3 H at 1.4 (triplet)
2 H at 4.35 (quartet)
3 H at 7.2 to 7.6 (broad peak)
1 H at 8.5 (singlet)

8.2 - 4a-amino-8-fluoro-2-methyl-1,2,3,4,4a,10a-hexahydro[10 H]benzopyrano[3,2-c]pyrid-10-ylacetic acid lactam $C_{15}H_{17}FN_2O_2$ Molecular weight=276.31
Prepared according to Example 5.1, starting with 80 g (0.339 mole) of ethyl 6-fluorocoumarin-3-carboxylate, 38.8 g (0.339 mole) N-methyl-4-piperidone, 52.4 g (0.678 mole) ammonium acetate and 2 liters of ethanol. Following recrystallization from isopropanol, the result is 37.5 g of 4a-amino-8-fluoro-2-methyl-1,2,3,4,4a,10a-hexahydro[10 H]benzopyrano[3,2-c]pyrid-10-ylacetic acid lactam (Yield=40%) Melting point$_G$=226°-228° C. IR$\nu_{C=O}$: 1680 cm$^{-1}$

| Analysis: | C% | H% | F% | N% |
|---|---|---|---|---|
| Calculated | 65.20 | 6.20 | 6.88 | 10.40 |
| Found | 64.83 | 6.09 | 7.20 | 10.49 |

EXAMPLE 9

4a-amino-2-acetyl-1,2,3,4,4a,10a-hexahydro[10 H]benzopyrano[3,2-c]pyrid-10-ylacetic acid lactam $C_{16}H_{18}N_2O_3$, molecular weight=286.32.

12.2 g (0.05 mole) of the product of Example 4 are dissolved in 200 mL of chloroform. 14 mL (0.1 mole) triethylamine are added, and 4.3 mL (0.06 mole) of acetyl chloride are added dropwise at 20° C. The solution is agitated for 6 hours at ambient temperature. It is washed with 400 mL of water, dried over sulfate, evaporated and recrystallized from a methanol-chloroform mixture. The result is 7.1 g of 4a-amino-2-acetyl-1,2,3,4,4a,10a-hexahydro[10 H]benzopyrano[3,2-c]pyrid-10-ylacetic acid lactam (Yield=50%) Melting point=284°-287° C.

IR$\nu_{C=O}$: 1680 cm$^{-1}$.

| Analysis: | C% | H% | N% |
|---|---|---|---|
| Calculated | 67.11 | 6.33 | 9.78 |
| Found | 66.82 | 6.05 | 9.98 |

EXAMPLE 10

7a-amino-10-methyl-7a,8,9,10,11,11a-hexahydro[12 H]benzo[f]benzopyrano[3,2-c]pyrid-12-ylacetic acid lactam $C_{19}H_{20}N_2O_2$, molecular weight=308.39

Prepared according to Example 5.1, starting with 70 g (0.261 mole) ethyl benzo[f]coumarin-3-carboxylate, 30 g (0.261 mole) of N-methyl-4-piperidone, 40.4 g (0.522 mole) ammonium acetate, and 1500 mL of ethanol. Following recrystallization from the mixture of ethyl and methyl acetates, the result is 44.2 g of 7a-amino-10-methyl-7a,8,9,10,11,11a,hexahydro[12 H]benzo[f]benzopyrano[3,2-c]pyrid-12-ylacetic acid lactam (Yield=55%) Melting point$_G$=263°-265° C., IR$\nu_{C=O}$: 1680 cm$^{-1}$

| Analysis: | C% | H% | N% |
|---|---|---|---|
| Calculated | 74.00 | 6.54 | 9.09 |
| Found | 73.91 | 6.46 | 8.96 |

EXAMPLE 11

4a-amino-2-(n-propyl)-1,2,3,4,4a,10a-hexhydro[10 H]benzopyrano[3,2-c]pyrid-10-ylacetic acid lactam $C_{17}H_{22}N_2O_2$, molecular weight=286.38.

A solution of 15 g (0.061 mole) of the product of Example 4 is kept for 10 hours at 80° C. in 300 mL of dimethyl formamide with 7.9 g (0.064 mole) of propyl bromide and 9.1 g (0.66 mole) potassium carbonate. The insolubles are filtered out, and the solvent evaporated under vacuum. Purification is carried out in ethyl acetate. The result is 9.9 g of 4a-amino-2-(n-propyl)-1,2,3,4,4a,10a,-hexahydro[10 H]benzopyrano[3,2-c]pyrid-10-ylacetic lactam (Yield=56.78%) Melting point$_G$=182°-184° C., IR$\nu_{C=O}$: 1680 cm$^{-1}$.

| Analysis: | C% | H% | N% |
| --- | --- | --- | --- |
| Calculated | 71.30 | 7.74 | 9.78 |
| Found | 71.02 | 7.59 | 9.66 |

EXAMPLE 12

4a-amino-2-(phenylpropyl)-1,2,3,4,4a,10a-hexahydro[10 H]benzopyrano[3,2-c]pyrid-10-ylacetic acid lactam $C_{23}H_{26}N_2O_2$, molecular weight = 362.47.

Prepared according to Example 11, from the product of Example 4 (15 g, 0.061 mole), 12.8 g (0.064 mole) of phenylpropyl bromide, producing 12.1 g of 4a-amino-2-(phenylpropyl)-1,2,3,4,4a,10a-hexahydro[10 H]benzopyrano[3,2-c]pyrid-10-ylacetic acid lactam, (Yield = 54.78%), melting point$_G$= 154°-156° C. (ethyl acetate), IR$\nu_{C=O}$: 1690 cm$^{-1}$

| Analysis: | C% | H% | N% |
| --- | --- | --- | --- |
| Calculated | 76.22 | 7.23 | 7.73 |
| Found | 75.97 | 7.01 | 7.62 |

EXAMPLE 13

4a-amino-2-dimethylaminopropyl-1,2,3,4,4a,10a-hexahydro[10 H]benzopyrano[3,2-c]pyrid-10-ylacetic acid lactam $C_{19}H_{27}N_3O_2$, molecular weight = 329.44.

Prepared according to Example 11 using the product of Example 4, 12.1 g (0.049 mole), 6.3 g (0.0516 mole) of 1-chlorodimethylaminopropane. The result is 7.6 g of 4a-amino-2-dimethylaminopropyl-1,2,3,4,4a,10a-hexahydro[10 H]benzopyrano[3,2-c]pyrid-10-ylacetic acid lactam. (Yield = 47%) Melting point$_G$= 149°-150° C. (ethyl acetate), IR$\nu_{C=O}$: 1680 cm$^{-1}$.

| Analysis: | C% | H% | N% |
| --- | --- | --- | --- |
| Calculated | 69.27 | 8.26 | 12.75 |
| Found | 68.92 | 8.01 | 12.93 |

EXAMPLE 14

4a-amino-7-chloro-2-methyl-1,2,3,4,4a,10a-hexahydro[10 H]benzopyrano[3,2-c]pyrid-10-ylacetic acid lactam $C_{15}H_{17}ClN_2O_2$, molecular weight 292.77.

14.1 Ethyl 7-chlorocoumarin-3-carboxylate $C_{12}H_9ClO_4$, molecular weight 252.5.

11.2 g (0.071 mole) of 4-chloro-2-hydroxybenzaldehyde, 12.5 g (0.072 mole) ethyl malonate, 30 mL ethanol, 0.4 L of piperidine and 0.1 mL of acetic acid are refluxed for 5 hours. The mixture of reactants is cooled to 0° C. and the resultant precipitate dried. It is washed in hexane, and the ethyl 7-chlorocoumarin-3-carboxylate is dried. Melting point$_G$= 122°14 123° C., IR$\nu_{C=O}$: 1760 cm$^{-1}$ (lactone and ester).

NMR (CDCl$_3$) p.p.m. relative to TMS
  3 H at 1.3 (triplet)
  2 H at 4.35 (quarter)
  3 H at 7.1 to 7.6 (broad peak)
  1 H at 9.45 (singlet).

14.2 4a-amino-6-chloro-2-methyl-1,2,3,4,4a,10a-hexahydro[10 H]benzopyrano[3,2-c]pyrid-10-ylacetic acid lactam Prepared according to Example 5.1, using 6.5 g (0.026 mole) ethyl 7-chlorocoumarin-3-carboxylate, 2.9 g (0.026 mole) N-methylpiperidone-4, 4 g (0.052 mole) ammonium acetate, and 150 mL ethanol. Following recrystallization in ethanol, the result is 3 g of the anticipated lactam (Yield = 40%). Melting point$_G$= 256°-258° C., IR$\nu_{C=O}$: 1675 cm$^{-1}$.

| Analysis: | C% | H% | Cl% | N% |
| --- | --- | --- | --- | --- |
| Calculated | 61.53 | 5.85 | 12.11 | 9.57 |
| Found | 61.34 | 5.86 | 12.40 | 9.63 |

EXAMPLE 15

4a-amino-8-nitro-2-methyl-1,2,3,4,4a,10a-hexahydro[10 H]benzopyrano[3,2-c]pyrid-10-ylacetic acid lactam.

$C_{15}H_{17}N_3O_4$, molecular weight = 303.32.

Prepared according to Example 5.1, starting with 70 g (0.27 mole) of ethyl 6-nitrocoumarin-3-carboxylate, 30.6 g (0.27 mole) of N-methyl-4-piperidone, 41.3 g (0.54 mole) ammonium acetate and 1.5 L of ethanol. After recrystallization from ethanol, the result is 38.8 g of 4a-amino-8-nitro-2-methyl-1,2,3,4,4a,10a-hexahydro[10 H]benzopyrano[3,2-c]pyrid-10-ylacetic acid lactam. (Yield = 47.4%) Melting point$_G$= 240°-242° C. IR$\nu_{C=O}$: 1680 cm$^{-1}$.

| Analysis: | C% | H% | N% |
| --- | --- | --- | --- |
| Calculated | 59.40 | 5.65 | 13.85 |
| Found | 59.25 | 5.66 | 13.74 |

EXAMPLE 16

4a,8-diamino-2-methyl-1,2,3,4,4a,10a-hexahydro[10 H]benzopyrano[3,2-c]pyrid-10-ylacetic acid lactam.

$C_{15}H_{19}N_3O_2$, molecular weight 273.34.

19.9 g (0.065 mole) of the product of Example 15 are placed in an autoclave with 300 mL of ethanol and 1 g of Pd/C at 10%. The autoclave was originally set to a hydrogen pressure of 60 kg/cm$^2$ and left for 3 hours at ambient temperature with agitation; it was then agitated for 2 hours at 50° C. After cooling, the palladium is filtered off, the filtrate is evaporated, and the resultant solid is recrystallized from a mixture of ethyl acetate and ethanol. The yield is 8.1 g of 4a,8-diamino-2-methyl-1,2,3,4,4a-hexahydro[10 H]benzopyrano[3,2-c]pyrid-10-ylacetic acid lactam. (Yield = 45.6%). Melting point$_G$= 230°-232° C. IR$\nu_{C=O}$: 1680 cm$^{-1}$.

| Analysis: | C% | H% | N% |
| --- | --- | --- | --- |
| Calculated | 65.91 | 7.01 | 15.37 |
| Found | 65.77 | 6.88 | 15.22 |

EXAMPLE 17

6,8-dichloro-4a-amino-2-methyl-1,2,3,4,4a,10a-hexahydro[10 H]benzopyrano[3,2-c]pyrid-10-ylacetic acid lactam.

$C_{15}H_{16}Cl_2N_2O_2$. Molecular weight=327.22.

Prepared according to Example 5.1 starting with 17.8 g (0.062 mole) of ethyl 6,8-dichlorocoumarin-3-carboxylate, 7.1 g (0.062 mole) N-methyl-4-piperidone, 9.5 g (0.124 mole) ammonium acetate and 800 mL ethanol. Following recrystallization from ethyl acetate, the result is 7.7 g of 6,8-dichloro-4a-amino-2-methyl-1,2,3,4,4a,10a-hexahydro[10 H]benzopyrano[3,2-c]pyrid-10-ylacetic acid lactam. (Yield=38%). Melting point$_G$=212°–216° C. IR$\nu_{C=O}$: 1680 cm$^{-1}$.

| Analysis: | C% | H% | Cl% | N% |
|---|---|---|---|---|
| Calculated | 55.05 | 4.93 | 21.57 | 8.56 |
| Found | 54.89 | 4.96 | 21.53 | 8.51 |

EXAMPLE 18

4a-amino-8-methoxy-2-methyl-1,2,3,4,4a,10a-hexahydro[10 H]benzopyrano[3,2-c]pyrid-10-ylacetic acid lactam.

$C_{16}H_{20}N_2O_3$. Molecular weight=288.35.

Prepared according to Example 5.1, starting with 35.5 g (0.143 mole) ethyl 6-methoxycoumarin-3-carboxylate, 16.4 g (0.143 mole) N-methyl-4-piperidone, 22.1 g (0.286 mole) ammonium acetate and 400 mL ethanol. By recrystallization from isopropanol, 26 g of 4a-amino-8-methoxy-2-methyl-1,2,3,4,4a,10a-hexahydro[10 H]benzopyrano[3,2-c]pyrid-10-ylacetic acid lactam are obtained.

(Yield=63%). Melting point$_G$=210°–212° C. IR$\nu_{C=O}$: 1680 cm$^{-1}$.

| Analysis: | C% | H% | N% |
|---|---|---|---|
| Calculated | 66.65 | 6.99 | 9.71 |
| Found | 66.61 | 6.89 | 9.67 |

EXAMPLE 19

4-amino-9-chloro-2-methyl-1,2,3,4,4a,10a-hexahydro[10 H]benzopyrano[3,2-c]pyrid-10-ylacetic acid lactam.

$C_{15}H_{17}ClN_2O_2$. Molecular weight=292.77.

19.1 Ethyl 5-chlorocoumarin-3-carboxylate $C_{12}H_9ClO_4$. Molecular weight 252.5.

15 g (0.0958 mole) of 2-chloro-6-hydroxy-benzaldehyde, 16.7 g (0.105 mole) ethyl malonate, 40 mL ethanol, 0.6 mL piperidine and 0.1 mL acetic acid are refluxed for 5 hours. After cooling the resultant product is dried. After drying, 14 g of ethyl 5-chlorocoumarin-3-carboxylate are obtained. (Yield=58%). Melting point$_G$=142°–144° C.

IR$\nu_{C=O}$: 1720 cm$^{-1}$.
$_{C=O}$: 1760 cm$^{-1}$.
NMR (CDCl$_3$)$\delta$ppm relative to TMS.
3 H at 1.45 (triplet)
2 H at 4.5 (quartet)
3 H from 7.1 to 7.7 (broad peak)
1 H at 8.8 (singlet).

19.2 4a-amino-9-chloro-2-methyl-1,2,3,4,4a,10a-hexahydro[10 H]benzopyrano[3,2-c]pyrid-10-ylacetic acid lactam.

$C_{15}H_{17}Cl N_2O_2$. Molecular weight=292.77.

Prepared according to Example 5.1 starting with 13.6 g (0.054 mole) ethyl 5-chlorocoumarin-carboxylate, 6.1 g (0.054 mole) N-methyl-4-piperidone, 8.3 g (0.108 mole) ammonium acetate and 250 mL of ethanol. After recrystallization from ethanol, 6.7 g of 4a-amino-9-chloro-2-methyl-1,2,3,4,4a,10a-hexahydro[10 H]benzopyrano[3,2-c]pyrid-10-ylacetic acid lactam are obtained. (Yield=42.4%). Melting point$_G$=241°–243° C. IR$\nu_{C=O}$: 1680 cm$^{-1}$.

| Analysis: | C% | H% | Cl% | N% |
|---|---|---|---|---|
| Calculated | 61.53 | 5.85 | 12.11 | 9.57 |
| Found | 61.36 | 5.76 | 11.98 | 9.61 |

EXAMPLE 20

4a-amino-6-chloro-2-methyl-1,2,3,4,4a,10a-hexahydro[10 H]benzopyrano[3,2-c]pyrid-10-ylacetic acid lactam.

$C_{15}H_{17}ClN_2O_2$. Molecular weight=292.77.

Prepared according to Example 5.1 starting with 12 g (0.048 mole) ethyl-8-chlorocoumarin-3-carboxylate, 5.5 g (0.048 mole) N-methyl-4-piperidone, 7.4 g (0.096 mole) ammonium acetate and 140 mL of ethanol. After recrystallization from isopropanol,6 g of 4a-amino-6-chloro-2-methyl-1,2,3,4,4a,10a-hexahydro[10 -H]benzopyrano[3,2-c]pyrid-10-ylacetic acid lactam are obtained. (Yield=43%). Melting point$_G$=206°–208° C. IR$\nu_{=O}$: 1680 cm$^{-1}$

| Analysis: | C% | H% | Cl% | N% |
|---|---|---|---|---|
| Calculated: | 61.53 | 5.85 | 12.11 | 9.57 |
| Found | 61.43 | 5.78 | 12.32 | 9.53 |

EXAMPLE 21

4a-amino-2-isopropyl-1,2,3,4,4a,10a-hexahydro[10 H]benzopyrano[3,2-c]pyrid-10-ylacetic acid lactam.

$C_{17}H_{22}N_2O_2$.Molecular weight=286.37.

Prepared according to Example 11, starting with 12.2 g (0.05 mole) of the product of Example 4, 9.35 g (0.055 mole) of isopropyl iodide. The result is 7.1 g of 4a-amino-2-isopropyl-1,2,3,4,4a,10a-hexahydro[10 H]benzopyrano[3,2-c]pyrid-10-yl-acetic acid lactam. (Yield=49.5%). Melting point$_G$=214°–216° C. IR$\nu_{C=O}$:1680 cm$^{-1}$.

| Analysis: | C% | H% | N% |
|---|---|---|---|
| Calculated | 71.30 | 7.74 | 9.78 |
| Found | 70.92 | 7.70 | 9.78 |

EXAMPLE 22

4a-amino-2-ethoxalyl-1,2,3,4,4a,10a-hexahydro[10 H]benzopyrano[3,2-c]pyrid-10-ylacetic acid lactam.

$C_{18}H_{20}N_2O_5$.Molecular weight=344.37.

A solution composed of 11.4 g (0.984 mole) of ethoxalyl chloride in 40 mL of chloroform is added to a solution of 17.1 g (0.07 mole) of the product of Example 4, 19.6 mL of triethylamine in 280 mL chloroform, keeping the temperature below 35° C. The mixture is left for 6 hours at room temperature. After rinsing with water, the organic phase is dried over $Na_2SO_4$, the solvent then evaporated and the residue recrystallized from methanol. The yield is 13.4 g of 4a-amino-2-ethoxalyl-1,2,3,4,4a,10a-hexahydro[10 H]benzopyrano[3,2-c]pyrid-10-ylacetic acid lactam. (Yield=55.5%).

Melting point$_G$=210°–212° C.
IR$\nu_{C=O}$: 1680 cm$^{-1}$(lactam).
:1730 cm$^{-1}$(ester).

| Analysis: | C% | H% | N% |
|---|---|---|---|
| Calculated | 62.78 | 5.85 | 8.13 |
| Found | 62.65 | 5.83 | 8.01 |

EXAMPLE 23

4a-amino-2-ethoxycarbonylmethyl-1,2,3,4,4a,10a-hexahydro[10 H]benzopyrano[3,2-c]pyrid-10-ylacetic acid lactam.

$C_{18}H_{33}N_2O_4$.Molecular weight=330.39.

Prepared according to Example 11, starting with 15 g (0.061 mole) of the product of Example 4 and 7.2 mL (0.064 mole) of ethyl bromoacetate. After recrystallization from ethanol, the yield is 12 g of 4a-amino-2-ethoxycarbonylmethyl-1,2,3,4,4a,10a-hexahydro[10 H]benzopyrano[3,2-c]pyrid-10-ylacetic acid lactam. (Yield=59.5%). Melting point$_G$=198°–200° C.

IR$\nu_{C=O}$:1680 cm$^{-1}$(lactam).
:1720 cm$^{-1}$(ester).

| Analysis: | C% | H% | N% |
|---|---|---|---|
| Calculated | 65.44 | 6.71 | 8.48 |
| Found | 65.51 | 6.59 | 8.46 |

EXAMPLE 24

4a-amino-2-allyl-1,2,3,4,4a,10a-hexahydro[10 H]benzopyrano[3,2-c]pyrid-10-ylacetic acid lactam.

$C_{17}H_{20}N_2O_2$.Molecular weight=284.36.

Prepared according to Example 11 starting with 15 g (0.061 mole) of the product of Example 4 and 8.1 g (0.067 mole) of allyl bromide. After recrystallization from isopropanol, the yield is 4.2 g of 4a-amino-2-allyl-1,2,3,4,4a,10a-hexahydro[10 H]benzopyrano[3,2c]pyrid-10-ylacetic acid lactam. (Yield=25%). Melting point$_G$=206°–208° C.

IR$\nu_{C=O}$:1680 cm$^{-1}$.

| Analysis: | C% | H% | N% |
|---|---|---|---|
| Calculated | 71.85 | 7.09 | 9.85 |
| Found | 71.61 | 7.01 | 9.74 |

EXAMPLE 25

4a-amino-2-cinnamoyl-1,2,3,4,4a,10a-hexahydro[10 H]benzopyrano[3,2-c]pyrid-10-ylacetic acid lactam.

$C_{23}H_{21}N_2O_3$.Molecular weight=374.43.

Prepared according to Example 9 starting with 8.5 g (0.035 mole) of the product of Example 4 and 7 g (0.042 mole) of cinnamoyl chloride. After recrystallization from ethanol, the yield is 7.4 g of 4a-amino-2-cinnamoyl-1,2,3,4,4a,10a-hexahydro[10 H]benzopyrano[3,2-c]pyrid-10-ylacetic acid lactam.
(Yield=56.5%).
Melting point$_G$=248°–250° C.
IR$\nu_{C=O}$:1680 cm$^{-1}$.

| Analysis: | C% | H% | N% |
|---|---|---|---|
| Calculated | 73.78 | 5.92 | 7.48 |
| Found | 73.72 | 5.98 | 7.40 |

EXAMPLE 26

4a-amino-2-benzyl-8-chloro-1,2,3,4,4a,10a-hexahydro[10 H]benzopyrano[3,2-c]pyrid-10-lacetic acid lactam.

$C_{21}H_{21}ClN_2O_2$.Molecular weight=368.88.

Prepared according to Example 5.1 starting with 292 g (1.15 mole) of ethyl 6-chlorocoumarin-3-carboxylate, 219 g (1.15 mole) of N-benzyl-4-piperidone, 178 g (2.31 mole) of ammonium acetate, and 4 L of ethanol. Following recrystallization from ethanol, the yield is 220.7 g of 4a-amino-2-benzyl-8-chloro-1,2,3,4,4a,10a-hexahydro[10 H]benzopyrano[3,2-c]pyrid-10-ylacetic acid lactam. (Yield=52%). Melting point$_G$=137°–139° C. IR$\nu_{C=O}$:1680 cm$^{-1}$.

| Analysis: | C% | H% | Cl% | N% |
|---|---|---|---|---|
| Calculated | 68.38 | 5.74 | 9.61 | 7.59 |
| Found | 68.14 | 5.63 | 9.48 | 7.44 |

EXAMPLE 27

4a-amino-8-chloro-2-ethoxycarbonyl-1,2,3,4,4a,10a-hexahydro[10 H]benzopyrano[3,2-c]pyrid-10-ylacetic acid lactam. $C_{17}H_{19}ClN_2O_4$.Molecular weight=350.81.

A solution composed of 21.7 g (0.2 mole) of ethyl chloroformate is refluxed in 20 mL of benzene. Then a solution composed of 22 g (0.06 mole) of the product of Example 26 in 150 mL of benzene is added dropwise. Refluxing is then carried out for 6 hours. After cooling, the mixture is washed with water and then with 3N HCl and water. After drying over $Na_2SO_4$, the solvents are evaporated. The residue is recrystallized from methanol. The yield is 16 g of 4a-amino-8-chloro-2-ethoxycarbonyl-1,2,3,4,4a,10a-hexahydro[10 H]benzopyrano[3,2-c]pyrid-10-ylacetic acid lactam.
(Yield=76%).
Melting point$_G$=226°–228° C.
IR$\nu_{C=O}$:1680 cm$^{-1}$.

| Analysis: | C% | H% | Cl% | N% |
|---|---|---|---|---|
| Calculated | 58.20 | 5.46 | 10.10 | 7.99 |
| Found | 58.04 | 5.52 | 9.63 | 7.72 |

EXAMPLE 28

4a-amino-8-chloro-2-methoxycarbonyl-1,2,3,4,4a,10a-hexahydro[10 H]benzopyrano[3,2-c]pyrid-10-ylacetic acid lactam.

$C_{16}H_{17}ClN_2O_4$.Molecular weight=336.77.

Prepared according to Example 27 starting with 22 g (0.06 mole) of the product of Example 26 and 21.7 g (0.2 mole) of methyl chloroformate. Following recrystallization from ethanol, the yield is 8.3 g of 4a-amino-8-chloro-2-methoxycarbonyl-1,2,3,4,4a,10a-hexahydro[10H]benzopyrano[3,2-c]pyrid-10-ylacetic acid lactam.

Yield=41%.

Melting point $_G$=165°–167° C.

IR$\nu_{C=O}$: 1680 cm$^{-1}$.

| Analysis: | C% | H% | Cl% | N% |
|---|---|---|---|---|
| Calculated | 57.06 | 5.09 | 10.53 | 8.32 |
| Found | 57.20 | 5.14 | 10.66 | 8.23 |

EXAMPLE 29

4a-amino-8-chloro-2-butoxycarbonyl-1,2,3,4,4a,10a-hexahydro[10H]benzopyrano[3,2-c]pyrid-10-ylacetic acid lactam.

$C_{19}H_{23}ClN_2O_4$. Molecular weight=378.85.

Prepared according to Example 27 starting with 17 g (0.046 mole) of the product of Example 26 and 21.2 g (0.155 mole) of n-butyl chloroformate. Following recrystallization from ethyl acetate, the yield is 10.2 g of 4a-amino-8-chloro-2-butoxycarbonyl-1,2,3,4,4a,10a-hexahydro[10H]benzopyrano[3,2-c]pyrid-10-ylacetic acid lactam.

(Yield=58.5%).

Melting point$_G$=144°–145° C.

IR$\nu_{C=O}$:1680 cm$^{-1}$.

| Analysis: | C% | H% | Cl% | N% |
|---|---|---|---|---|
| Calculated | 60.24 | 6.12 | 9.36 | 7.39 |
| Found | 60.29 | 6.17 | 9.32 | 7.31 |

EXAMPLE 30

4a-amino-8-chloro-2-(2,2,2-trifluoroethoxycarbonyl)-1,2,3,4,4a,10a-hexahydro[10H]benzopyrano[3,2-c]pyrid-10-ylacetic acid lactam.

$C_{17}H_{16}ClF_3N_2O_4$. Molecular weight=404.78.

Prepared according to Example 27 starting with 5.9 g (0.02 mole) of the product of Example 5.1 and 13.2 g (0.066 mole) of trifluoroethyl chloroformate. Following recrystallization from isopropanol, the yield is 3 g of 4a-amino-8-chloro-2-(2,2,2-trifluoroethoxycarbonyl)-1,2,3,4,4a,10a-hexahydro[10H]benzopyrano [3,2-c]pyrid-10-ylacetic acid lactam.

(Yield=37%).

Melting point$_G$=194°–196° C.

IR$\nu_{C=O}$:1690 cm$^{-1}$(lactam).

:1720 cm$^{-1}$ (carbamate).

| Analysis: | C% | H% | Cl% | F% | N% |
|---|---|---|---|---|---|
| Calculated | 50.44 | 3.98 | 8.76 | 14.08 | 6.92 |
| Found | 50.33 | 3.94 | | 14.18 | 6.83 |

EXAMPLE 31

4a-amino-8-chloro-2-(2-ethylhexyloxycarbonyl)-1,2,3,4,4a,10a-hexahydro[10H]benzopyrano[3,2-c]pyrid-10-ylacetic acid lactam.

$C_{23}H_{31}ClN_2O_4$. Molecular weight=434.96.

Prepared according to Example 27 starting with 12.2 g (0.0416 mole) of the product of Example 5.1 and 26.7 g (0.139 mole) of 2-ethylhexyl chloroformate. Following recrystallization in acetone, the yield is 8.1 g of 4a-amino-8-chloro-2-(2-ethylhexyloxycarbonyl)-1,2,3,4,4a,10a-hexahydro[10H]benzopyrano[3,2-c]pyrid-10-ylacetic acid lactam. (Yield=44.8%). Melting point$_G$=140°–142° C.

IR$\nu_{C=O}$:1690 cm$^{-1}$(lactam).

:1710 cm$^{-1}$(carbamate).

| Analysis: | C% | H% | Cl% | N% |
|---|---|---|---|---|
| Calculated | 63.51 | 7.18 | 8.15 | 6.44 |
| Found | 63.46 | 7.11 | 8.23 | 6.33 |

EXAMPLE 32

4a-amino-8-chloro-2-cyclohexyloxycarbonyl-1,2,3,4,4a,10a-hexahydro[10H]benzopyrano[3,2-c]pyrid-10-ylacetic acid lactam.

$C_{21}H_{25}ClN_2O_4$. Molecular weight=404.89.

Prepared according to Example 27 starting with 12.2 g (0.0416 mole) of the product of Example 5.1 and 22.6 g (0.139 mole) of cyclohexyl chloroformate. Following recrystallization in ethanol, the yield is 7.2 g of 4a-amino-8-chloro-2-cyclohexyloxycarbonyl-1,2,3,4,4a,10a-hexahydro[10H]benzopyrano[3,2-c]Pyrid-10-ylacetic acid lactam.

(Yield=42.7%).

Melting point$_G$=222°–224° C.

IR$\nu_{C=O}$:1690 cm$^{-1}$.

| Analysis: | C% | H% | Cl% | N% |
|---|---|---|---|---|
| Calculated | 62.29 | 6.22 | 8.75 | 6.92 |
| Found | 62.43 | 6.22 | 8.80 | 6.87 |

EXAMPLE 33

4a-amino-8-chloro-2-benzyloxycarbonyl-1,2,3,4,4a,10a-hexahydro[10H]benzopyrano[3,2-c]pyrid-10-ylacetic acid lactam.

$C_{22}H_{21}ClN_2O_4$. Molecular weight=412.86.

Prepared according to Example 27 starting with 39.6 g (0.1 mole) of the product of Example 26 and 56.5 g (0.33 mole) benzyl chloroformate. Following recrystallization from ethyl acetate, the yield is 19 g of 4a-amino-8-chloro-2-benzyloxycarbonyl-1,2,3,4,4a,10a-hexahydro[10H]benzopyrano[3,2-c]pyrid-10-ylacetic acid lactam.

(Yield=46%).

Melting point$_G$=228°–230° C.

IR$\nu_{C=O}$:1680 cm$^{-1}$ (lactam)

: 1720 cm$^{-1}$(carbamate)

| Analysis: | C% | H% | Cl% | N% |
|---|---|---|---|---|
| Calculated | 64.02 | 5.12 | 8.58 | 6.78 |
| Found | 63.85 | 5.28 | 8.31 | 6.62 |

EXAMPLE 34

4a-amino-8-chloro-1,2,3,4,4a,10a-hexahydro[10H]benzopyrano [3,2-c]pyrid-10-ylacetic acid lactam.

$C_{14}H_{15}ClN_2O_2$. Molecular weight=278.73.

27.8 g (0.06 mole) of the product of Example 33 are dissolved in 400 cc of chloroform and then bubbled with hydrobromic acid (obtained by heating 62% aqueous solution to 50° C.) for 30 minutes, at ambient temperature. A precipitate forms. It is filtered off, dissolved in 3 L of water, and made alkaline with 10% NaOH. Cooling yields a precipitate. The latter is dried and recrystallized from methanol. The yield is 10 g of 4a-amino-8-chloro-1,2,3,4,4a,10a-hexahydro[10 H]benzopyrano[3,2-c]pyrid-10-ylacetic acid lactam.
(Yield=59.8%).
Melting point $_G$=252°-254° C.
IR $\nu_{C=O}$: 1680 cm$^{-1}$.

| Analysis: | C% | H% | Cl% | N% |
|---|---|---|---|---|
| Calculated | 60.33 | 5.42 | 12.72 | 10.05 |
| Found | 60.32 | 5.30 | 12.57 | 10.08 |

EXAMPLE 35

4a-amino-8-chloro-2-phenyl-1,2,3,4,4a,10a-hexahydro[10 H]benzopyrano[3,2-c]pyrid-10-ylacetic acid lactam.

$C_{20}H_{19}ClN_2O_2$. Molecular weight=354.83.

Prepared according to Example 5.1 starting with 16.9 g (0.067 mole) of ethyl 6-chlorocoumarin-3-carboxylate, 11.7 g (0.067 mole) of N-phenyl-4-piperidone, 10.5 g (0.134 mole) of ammonium acetate and 380 mL of ethanol. Recrystallization from methanol yields 9.5 g of 4a-amino-8-chloro-2-phenyl-1,2,3,4,4a,10a-hexahydro[10 H]benzopyrano[3,2-c]pyrid-10-ylacetic acid lactam.
(Yield=40%).
Melting point$_G$=220°-222° C. IR$_\nu$ $_{C=O}$: 1680 cm$^{-1}$.

| Analysis: | C% | H% | Cl% | N% |
|---|---|---|---|---|
| Calculated | 67.70 | 5.40 | 9.99 | 7.89 |
| Found | 67.83 | 5.48 | 9.86 | 7.86 |

EXAMPLE 36

8-chloro-2-methyl-4a-methylamino-1,2,3,4,4a,10a-hexahydro[10 H]benzopyrano[3,2-c]pyrid-10-ylacetic acid lactam.

$C_{16}H_{19}ClN_2O_2$. Molecular weight=306.79.

33 g (0.125 mole) of ethyl 6-chlorocoumarin-3-carboxylate, 14.3 g of N-methyl-4-piperidone, 24 g of methylamine (0.25 mole) in a 33% solution in ethanol and 550 mL of ethanol are placed in an autoclave. The mixture is held at 70°-80° C. for 7 hours. After cooling, it is processed as in Example 5.1. After recrystallization from ethanol, the yield is 13 g of 8-chloro-2-methyl-4a-methylamino-1,2,3,4,4a,10a-hexahydro[10 H] benzopyrano[3,2-c] pyrid-10-ylacetic acid lactam. (Yield=34%).
Melting point$_G$=158°160° C.
IR$_\nu$ $_{C=O}$: 1680 cm$^{-1}$.

| Analysis: | C% | H% | Cl% | N% |
|---|---|---|---|---|
| Calculated | 62.54 | 6.24 | 11.56 | 9.13 |
| Found | 62.70 | 6.36 | 11.48 | 9.20 |

EXAMPLE 37

2-methyl-4a-methylamino-1,2,3,4,4a,10a-hexahydro[10 H] benzopyrano[3,2-c]-10-ylacetic acid lactam.

$C_{16}H_{20}N_2O_2$. Molecular weight=272.34.

Prepared according to Example 36, starting with 27.3 g (0.125 mole) ef ethyl coumarin-3-carboxylate, 14.3 g of N-methyl-4-piperidone, 24 g (0.25 mole) of methylamine in 33% ethanol solution and 500 mL of ethanol. The result is a crude base which it has not been possible to recrystallize: 25 g
citrate $C_{22}H_{28}N_2O_9$. Molecular weight=464.48.

The 25 g of crude product are dissolved in 120 mL of acetone, and a solution of 19.2 g (0.1 mole) of citric acid in 200 ml of acetone is added with cooling. The product obtained is dried and recrystallized from ethanol. The yield is 14 g of 2 methyl-4a-methylamino-1,2,3,4,4a,10a-hexahydro[10 H] benzopyrano[3,2-c]pyrid-10-ylacetic acid lactam citrate. (Yield=26%).
Melting point$_G$=180°-182° C.
IR$_\nu$ $_{C=O}$: 1690 cm$^{-1}$.

| Analysis: | C% | H% | N% |
|---|---|---|---|
| Calculated: | 56.89 | 6.07 | 6.03 |
| Found: | 56.69 | 5.97 | 5.92 |

EXAMPLE 38

4a-benzylamino-2-methyl-8-chloro-1,2,3,4,4a,10a-hexahydro[10 H] benzopyrano[3,2-c]pyrid-10-ylacetic acid lactam.

$C_{22}H_{23}ClN_2O_2$.
Molecular weight=382.88.
Prepared according to Example 5.1 starting with 25.2 g (0.1 mole) of ethyl 6-chlorocoumarin-3-carboxylate, 11.5 g (0.1 mole) N-methyl-4-piperidone, 21.4 g (0.2 mole) of benzylamine and 500 mL ethanol. After recrystallization from diisopropyl ether the yield is 9.5 g of 4a-benzylamino-2-methyl-8-chloro-1,2,3,4,4a,10a-hexahydro[10 H] benzopyrano[3,2-c]pyrid-10-ylacetic acid lactam.
(Yield=25%).
Melting point$_G$=115°-117° C.
IR$_\nu$ $_{C=O}$: 1690 cm$^{-1}$.

| Analysis: | C% | H% | Cl% | N% |
|---|---|---|---|---|
| Calculated: | 69.01 | 6.05 | 9.26 | 7.32 |
| Found: | 69.14 | 6.15 | 9.07 | 7.17 |

EXAMPLE 39

4a-amino-8-chloro-2-(2,2,2-trichloroethoxycarbonyl)-1,2,3,4,4a,10a-hexahydro[10 H] benzopyrano[3,2-c]pyrid-10-ylacetic acid lactam.

$C_{17}H_{16}Cl_4N_2O_4$. Molecular weight=454.14.
Prepared according to Example 27 starting with 12.2 g (0.0416 mole) of the product according to Example 5.1 and 29.5 g (0.139 mole) of trichloroethyl chloroformate. By recrystallization from ethyl acetate, the yield is 8.4 g of 4a-amino-8-chloro-2-(2,2-trichloroethoxycarbonyl)-1,2,3,4,4a,10a-hexahydro[10 H] benzopyrano[3,2-c]pyrid-10-ylacetic acid lactam.
(Yield=44.5%).
Melting point=223°-225° C.
IR$_{84}$ $_{C=O}$: 1695 cm$^{-1}$ (lactam)
: 1720 cm$^{-1}$ (carbamate)

| Analysis: | C% | H% | Cl% | N% |
|---|---|---|---|---|
| Calculated: | 44.96 | 3.55 | 31.23 | 6.16 |

| Analysis: | C% | H% | Cl% | N% |
|---|---|---|---|---|
| Found: | 45.12 | 3.38 | 31.46 | 5.92 |

EXAMPLE 40

4a-amino-2-benzoyl-1.2.3.4.4a.10a-hexahydro[10 H] benzopyrano[3,2-c]pyrid-10-ylacetic acid lactam.

$C_{21}H_{20}N_2O_3$. Molecular weight=348.40.

Prepared according to Example 9 starting with 8.5 g (0.035 mole) of the product of Example 4 and 5.9 g (0.042 mole) of benzoyl chloride. Recrystallization from ethanol yields 8.2 g of 4a-amino-2-benzoyl-1.2.3.4.4a.10a-hexahydro[10 H] benzopyrano [3.2-c]pyrid-10-ylacetic acid lactam.

(Yield=67%).
Melting point$_G$=253°-255° C.
IR$_{\nu\ C=O}$: 1680 cm$^{-1}$.

| Analysis: | C% | H% | N% |
|---|---|---|---|
| Calculated | 72.40 | 5.78 | 8.04 |
| Found | 72.20 | 5.51 | 7.91 |

EXAMPLE 41

4a-amino-2-pivaloyl-1,2,3,4,4a,10a-hexahydro[10 H] benzopyrano [3,2-c]pyrid-10-ylacetic acid lactam.

$C_{19}H_{24}N_2O_3$. Molecular weight=328.41.

Prepared according to Example 9 starting with 8.5 g (0.035 mole) of the product of Example 4 and 5.1 g (0.042 mole) of pivaloylchloride. After recrystallization from isopropanol, the yield is 6.6 g of 4a-amino-2-pivaloyl-1,2,3,4,4a,10a-hexahydro[10 H] benzopyrano[3,2-c]pyrid-10-ylacetic acid lactam.

(Yield=57.5%).
Melting point$_G$=253°-255° C.
IR$_{\nu\ C=O}$: 1690 cm$^{-1}$.

| Analysis: | C% | H% | N% |
|---|---|---|---|
| Calculated: | 69.49 | 7.36 | 8.53 |
| Found: | 69.62 | 7.51 | 8.74 |

EXAMPLE 42

4a-amino-2-acetyl-8-chloro 1,2,3,4,4a,10a-hexahydro[10 H]benzopyrano[3,2-c]pyrid-10-ylacetic acid lactam.

$C_{16}H_{17}ClN_2O_3$. Molecular weight=320.77.

Prepared according to Example 9 with 4.5 g (0.016 mole) of the product of Example 34 and 2 g (0.026 mole) acetyl chloride. Following recrystallization from a mixture of methanol and ethyl acetates, the yield is 2.7 g of 4a-amino-2-acetyl-8-chloro 1,2,3,4,4a,10a-hexahydro[10H] benzopyrano[3,2-c]pyrid-10-ylacetic acid lactam.

(Yield=52.6%).
Melting point$_G$=255°-257° C.
IR$_{\nu\ C=O}$: 1670 cm$^{-1}$
: 1690 cm$^{-1}$

| Analysis: | C% | H% | Cl% | N% |
|---|---|---|---|---|
| Calculated: | 59.91 | 5.34 | 11.05 | 8.73 |
| Found: | 60.12 | 5.51 | 11.32 | 9.01 |

EXAMPLE 43

4a-amino-8-chloro-2-isopropyl-1,2,3,4,4a,10a-hexahydro[10 H] benzopyrano[3,2-c]pyrid-10-ylacetic acid lactam. $C_{17}H_{21}ClN_2O_2$. Molecular weight: 320.82.

Prepared according to Example 11 starting with 6.2 g (0.022 mole) of the product of Example 34 and 3.1 g of 2-bromopropane. Following recrystallization from ethanol, the yield is 2 g of 4a-amino-8-chloro-2-isopropyl-1.2.3.4.4a.10a-hexahydro[10H] benzopyrano[3,2-c]pyrid-10-ylacetic acid lactam. (Yield=28%). Melting point$_G$=186°-188° C.
IR$_{\nu\ C=O}$: 1680 cm$^{-1}$

| Analysis: | C% | H% | Cl% | N% |
|---|---|---|---|---|
| Calculated: | 63.65 | 6.60 | 11.05 | 8.73 |
| Found: | 63.44 | 6.39 | 10.88 | 8.55 |

EXAMPLE 44

4a-amino-8-chloro-2-(2-methyl-3-propenyl)-1,2,3,4,4a,10a-hexahydro[10 H] benzopyrano[3,2-c]pyrid-10-ylacetic acid lactam.

$C_{18}H_{21}ClN_2O_2$. Molecular weight=332.83.

Prepared according to Example 11 starting with 6.2 g (0.022 mole) of the product of Example 34 and 2.6 mL (0.025 mole) of 3-chloro-2-methylpropene. Recrystallization from ethyl acetate yields 2.3 g of 4a-amino-8-chloro-2-(2-methyl-3-propenyl)-1,2,3,4,4a,10a-hexahydro[10 H] benzopyrano]3,2-c] pyrid-10-ylacetic acid lactam.

(Yield=31.5%).
Melting point$_G$=202°-204° C.
IR$_{\nu\ C=O}$: 1680 cm$^{-1}$.

| Analysis: | C% | H% | Cl% | N% |
|---|---|---|---|---|
| Calculated: | 64.95 | 6.36 | 10.65 | 8.42 |
| Found: | 65.12 | 6.47 | 10.72 | 8.51 |

It will be obvious to those skilled in the art that various changes may be made without departing from the scope of the invention and the invention is not to be considered limited to what is described in the specification.

What is claimed is:

1. Substituted hexahydrobenzopyrano[3,2-c]pyridine, of the formula

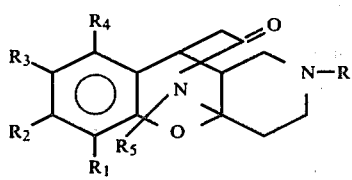

where R is hydrogen or a saturated or unsaturated, linear or branched, lower alkyl, lower phenylalkyl, phenylcarbonyl, cinnamoyl, benzyloxycarbonyl, diloweralkylaminoloweralkyl, lower alkyl carbonyl, loweralkoxycarbonyl, haloethoxycarbonyl, cycloloweralkyloxycarbonyl or phenyl; $R_1$ is hydrogen, halogen, or lower alkoxy; $R_2$ is hydrogen or halogen; $R_3$ is hydrogen, halogen, lower alkyl, lower alkoxy, nitro or amino, or forms naphthalene with $R_4$ and the benzene ring; $R_4$ is hydrogen, halogen, or forms naphthalene with $R_3$ and the benzene ring; $R_5$ is hydrogen, lower alkyl, or benzyl; or a salt thereof with a mineral or organic acid, acceptable for treating human beings.

2. A compound in accordance with claim 1, wherein R is trihaloethoxycarbonyl or cyclohexyloxycarbonyl.

3. A compound in accordance with claim 1, wherein $R_3$ is methoxy.

4. 4a-amino-2-methyl-1,2,3,4,4a,10a-hexahydro[10 H] benzopyrano[3,2-c]pyrid-10-ylacetic acid lactam in accordance with claim 1.

5. 4a-amino-8-chloro-2-methyl-1,2,3,4,4a,10a-hexahydro [10 H]benzopyrano[3,2-c]pyrid-10-ylacetic acid lactam in accordance with claim 1.

6. Lactam of the ethyl monoester of 4a-amino-8-chloro-2-methyl-1,2,3,4,4a,10a-hexahydro[10H]benzopyrano[3,2-c]pyrid-10ylmalonic acid.

7. 4a-amino-8-bromo-2methyl-1,2,3,4,4a,10a-hexahydro [10 H] benzopyrano[3,2-c]pyrid-10-ylacetic acid lactam in accordance with claim 1.

8. 4a-amino-2-8-dimethyl-1,2,3,4,4a,10a-hexahydro[10 H] benzopyrano[3,2-c]pyrid-10-ylacetic acid lactam in accordance with claim 1.

9. 4a-amino-8-fluoro-2-methyl-1,2,3,4,4a,10a-hexahydro[10 H]benzopyrano[3,2-c]pyrid-10-ylacetic acid lactam in accordance with claim 1.

10. 4a-amino-2-acetyl-1,2,3,4,4a,10a-hexahydro[10 H] benzopyrano[3,2-c]pyrid-10-ylacetic acid lactam in accordance with claim 1.

11. 7a-amino-10-methyl-7a,8,9,10,11,11a-hexahydro[12 H] benzo[f]benzopyrano[3,2-c]pyrid-12-ylacetic acid lactam in accordance with claim 1.

12. 4a-amino-8-nitro-2-methyl-1,2,3,4,4a,10a-hexahydro[10 H]benzopyrano[3,2-c]pyrid-10-ylacetic acid lactam in accordance with claim 1.

13. 4a-amino-8-methoxy-2-methyl-1,2,3,4,4a,10a-hexahydro[10 H]benzopyrano[3,2-c]pyrid-ylacetic acid lactam in accordance with claim 1.

14. 4a-amino-8-chloro-2-ethoxycarbonyl-1,2,3,4,4a,10a-hexahydro[10 H]benzopyrano[3,2-c]pyrid-10-ylacetic acid lactam in accordance with claim 1.

15. 4a-amino-8-chloro-2-methoxycarbonyl-1,2,3,4,4a,10a-hexahydro[10 H]benzopyrano[3,2-c]pyrid-10-ylacetic acid lactam in accordance with claim 1.

16. 8-chloro-2-methyl-4a-methylamino-1,2,3,4,4a,10a-hexahydro[10 H]benzopyrano[3,2-c]pyrid-10-ylacetic acid lactam in accordance with claim 1.

17. 4a-amino-8-chloro-1,2,3,4,4a,10a-hexahydro[10 H] benzopyrano [3,2-c] pyrid-10-ylacetic acid lactam in accordance with claim 1.

18. 4a-amino-8-chloro-2-isopropyl-1,2,3,4,4a,10a-hexahydro[10 H]benzopyrano[3,2-c] pyrid-10-ylacetic acid lactam in accordance with claim 1.

19. 4a-amino-2-ethoxalyl-1,2,3,4,4a,10a-hexahydro[10 H] benzopyrano [3,2-c] pyrid-10-ylacetic acid lactam.

20. 4a-amino-2-ethoxycarbonylmethyl-1,2,3,4,4a,10a-hexahydro [10 H] benzopyrano [3,2-c] pyrid-10-ylacetic acid lactam.

21. A pharmaceutical composition useful as an antidepressant, comprising as the active principal, an amount sufficient for antidepressant activity of a hexahydrobenzopyrano [3,2-c]pyridine according to claim 1, and a pharmaceutically acceptable diluent or carrier.

* * * * *